United States Patent [19]

Moriya et al.

[11] Patent Number: 5,010,879
[45] Date of Patent: Apr. 30, 1991

[54] DEVICE FOR CORRECTING SPINAL DEFORMITIES

[75] Inventors: Hideshige Moriya; Hiroshi Kitahara; Shohei Minami, all of Chiba, Japan; Keijiro Isobe, Ontario, Canada; Yoshinori Nakata, Chiba; Chiaki Tanaka, Tokyo, both of Japan

[73] Assignee: Tanaka Medical Instrument Manufacturing Co., Japan

[21] Appl. No.: 422,562

[22] Filed: Oct. 17, 1989

[30] Foreign Application Priority Data

Mar. 31, 1989 [JP] Japan .................... 1-82019

[51] Int. Cl.⁵ .................... A61F 5/00; A61F 5/04
[52] U.S. Cl. .................... 128/69; 606/61
[58] Field of Search .............. 128/68, 69, 71, 75, 128/78; 606/61

[56] References Cited

U.S. PATENT DOCUMENTS

| 4,404,967 | 9/1983 | Bacal et al. | 606/61 |
| 4,422,451 | 12/1983 | Kalamchi | 606/61 |
| 4,433,676 | 2/1984 | Bobechko | 606/61 |
| 4,641,636 | 2/1987 | Cotrel | 606/61 X |
| 4,773,402 | 9/1988 | Asher et al. | 128/69 |

FOREIGN PATENT DOCUMENTS

| 3032237 | 3/1982 | Fed. Rep. of Germany | 128/69 |
| 2487669 | 2/1982 | France | 128/69 |

Primary Examiner—Richard J. Apley
Assistant Examiner—Linda C. M. Dvorak
Attorney, Agent, or Firm—Lowe, Price, LeBlanc, Becker & Shur

[57] ABSTRACT

A device for correcting spinal deformities by attachment to portions of the spine of a patient has an elongated rod with a smooth outer peripheral surface, hook members each of which is formed with a hook-like engagement member on one end and a retaining portion through which the elongated rod is loosely inserted, and wedge-like members each in the form of a cylinder with a slit which is provided with a flange on one end. After the elongated rod is loosely inserted into the retaining portions of said hook members with a predetermined play, the wedge-like members mounted on the elongated rod are forcibly inserted into interstices formed between the loosely fitted rod and hook members, to thereby firmly fix the hook members with the elongated rod.

9 Claims, 3 Drawing Sheets

DEVICE FOR CORRECTING SPINAL DEFORMITIES

BACKGROUND OF THE INVENTION

1. Field of the Invention

This invention relates to a device suitable for correcting spinal deformities and for use in treatments for correcting various spinal deformities of congenital or acquired type.

2. Background of the Prior Art

A device of the kind shown in FIG. 7 is generally used in procedures to correct congenital or acquired spinal deformities due to scoliosis, kyphosis, spinal caries, spondylolisthesis and injury of the spine.

The device 31 per FIG. 7 comprises a distraction rod 37, having a length sufficient to correct the curved or deformed spine to a predetermined shape, and hook members 32 which are attached on the distraction rod 37 to be engaged with the transversal projection or vertebral arch of a patient.

The distraction rod 37 is formed of metal in a substantially linear form, and is knurled on the outer surface to give an irregularly textured portion 38 thereto.

Each hook member 32 includes a main body 32a in a substantially rectangular form with a hook 33 on one side thereof, a retaining groove (or retaining hole) 34 for inserting and retaining the distraction rod 37 within the main body 32a on the side opposite to the hook 33, and a lock bolt 36 for fixing the rod 37 when it is inserted in the hole 34 at a predetermined position.

The device 31 is fixed to a patient by engaging at least two hook members 32, 32 with transversal projections or portions of the vertebral arch of the spine which are exposed by surgery for gradually pulling or stretching the deformed spine to a predetermined shape, and inserting the distraction rod 37 through the holes or grooves 34 of the hooks 32, 32 for maintaining the spine in a corrected state. Fixing bolts 36, 36 are then tightened to support the pulled or stretched spine, and the muscular tunics, the fascia, and the skin of the patient are sutured so that the fixed state of the device may be maintained for a given period. Through-hole 35 is provided to secure insertion and engagement of the hook member 32 at a predetermined location on the spine with hookholders.

The prior art device mentioned above is an improvement made on a spinal deformity correction device which was developed by Paul R. Harrington in Houston Texas, USA in 1962, and has been widely used.

The known spinal deformity correction device with the above-mentioned structure has a knurled surface on the outer periphery of the distraction rod so as to enable secure engagement of the hook member when fixing bolts are inserted. The knurled rod, on the other hand, may have an adverse effect on the human body and may lower the rigidity of the whole rod. The knurled surface moreover, prevents hook members from smoothly sliding on the rod due to high frictional resistance.

As this device has the hook members fixed on the rod by tightening bolts, the operation of tightening/loosening the bolts is quite cumbersome.

The prior art device is inconvenient to use in that the knurled surface increases resistance, causes extra difficulties, and prolongs the recovery time.

There is, therefore, a need for a more effective and advantageous spinal deformity correction device.

SUMMARY OF THE INVENTION

It is a principal object of this invention to eliminate problems encountered in known spinal deformity correction devices and to provide a device for correcting spinal deformities which is extremely easy to handle, either does not or hardly harms the patient's body, and minimizes the treatment time.

In order to achieve these and other related objects, the spinal deformity correction device according to a preferred embodiment of this invention comprises an elongated rod with a smooth peripheral surface, hook members each having a hook engagement member on one side thereof and a retaining groove through which said elongated rod may be inserted with a predetermined play, and a wedge member in the form of a cylinder having a slit and a flange on one end thereof, the device being structured so that the elongated rod is inserted through said hook members in the retaining grooves with said play, and the wedge members mounted on said elongated rod are forcibly fit within the play to thereby fix said hook members to the elongated rod at selected locations.

The elongated rod is preferably made of a rust-proof steel material such as stainless steel or the like. So far as the surface thereof is smooth, there are no specific restrictions on its diameter or its length, but it should preferably have a diameter sufficient to endure a load of 60 kg or higher in a deflection test.

It is desirable that the hook member be formed by molding of a material similar to that of the elongated rod. So far as each hook member has a retaining means comprising a groove through which the elongated rod is loosely inserted and a hook engagement member on one side thereof for engaging with the spine, there is no other specific limitation on the shape or form of the rest of the device.

The wedge member preferably is formed as a cylinder with a slit and a flange on one end thereof, and is preferably molded from material similar to that of the elongated rod and hook member.

The slit may be on a side wall of the cylindrical member and need not necessarily extend to or through the flange. The engagement between the wedge member and the hook member may be made more secure simply by knurling the peripheral surface of the cylindrical member.

When an end of the cylindrical member is tapered, it facilitates insertion of the wedge member into the hook member.

The spinal deformity correction device according to a preferred embodiment of this invention comprises an elongated rod of an appropriate length and diameter and having a smooth peripheral surface, hook members each having a retaining member which allows the elongated rod to be inserted therethrough with a predetermined play and a hook-like engagement member on one side thereof, and wedge members in the form of cylinders each having a flange on one end thereof and a slit.

These three types of component members of the device are sequentially used and assembled during the treatment for correcting spinal deformities.

More particularly, plural hook members are hooked at predetermined positions on the transversal projections, spinal joints, or spinal arch of the deformed spine, and a separate outrigger member is used to correct the deformity between these hook members. Then, the elongated rod is securely affixed between these hook members for fixing and the outrigger device is removed, but the corrected state is maintained.

The use of the elongated rod which has a smooth peripheral surface instead of a knurled surface is advantageous in that it enhances safety for the patients and facilitates sliding between the rod and the hook members for easier handling.

As this device does not use bolts or nuts for fixing the rod with the hook members, and as it uses cylindrical wedge members each having a flange on one end and a slit thereon, the device enables the insertion of the rod through the hook members easily and firmly so as to completely avoid deviation of the hook members as might otherwise occur during use.

As the wedge members can be easily removed after correction, in practice this is done simply by fitting a separate dedicated device with the flanges of the cylindrical ends to pull out the wedge members which have been forcibly inserted through the retaining holes or grooves, thus allowing easy separation of the hook members from the rod.

BRIEF DESCRIPTION OF THE DRAWINGS

FIG. 1 shows a hook member, FIG. 2 a wedge member and FIG. 3 an elongated rod;

DESCRIPTION OF PREFERRED EMBODIMENT

An embodiment of the spinal deformity correction device according to this invention will now be described in further detail, referring to the attached drawings.

Figure 1:
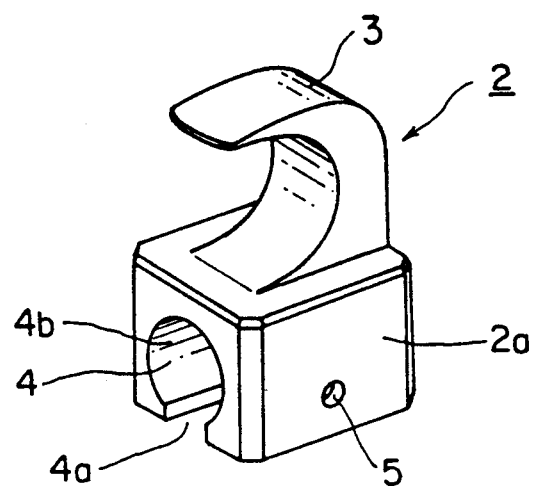
FIGS. 1 through 3 are perspective views of component parts of the spinal deformity correction device according to a preferred embodiment of this invention and, specifically.
Figure 2:
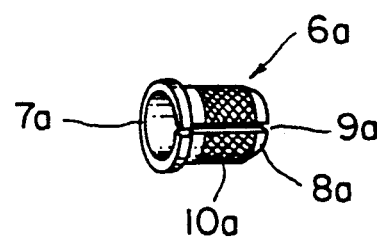
Figure 3:
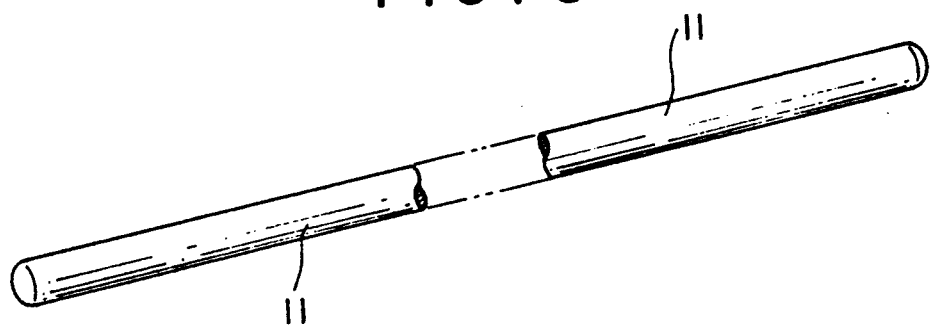
Figure 4:
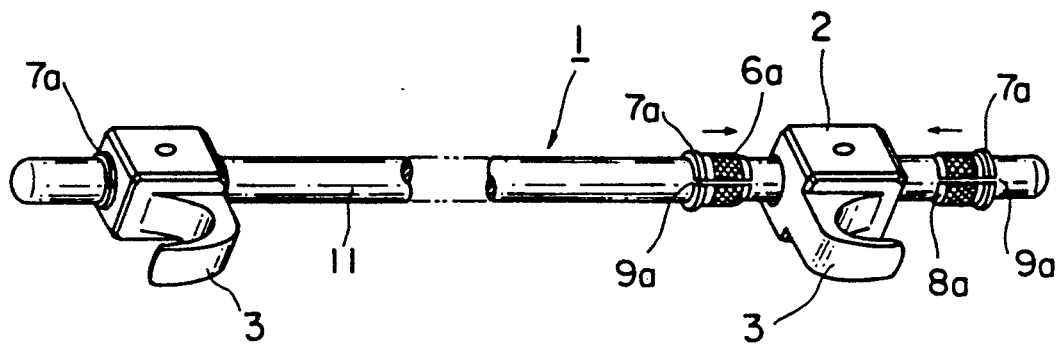
FIG. 4 is a perspective view to show the assembled state of the device.

In a preferred embodiment, the device 1 comprises a hook member 2 shown in FIG. 1, a wedge member 6a shown in FIG. 2 and an elongated rod 11 shown in FIG. 3.

As shown in FIG. 1, the hook member 2 comprises a cubic main body 2a from one side surface of which projects a hook-like engagement member 3 with a curved tip end. The main body 2a is formed to have a retaining groove 4 on a lower surface thereof under the member 3 through which an elongated rod 11 is forcibly inserted in the longitudinal direction.

The groove 4 comprises an opening 4a, through which the elongated rod 11 may be inserted along the axial direction of the grove 4 and a retaining member 4b extending from said opening 4a for holding the rod 11 with play.

The retaining member 4b may alternatively be a hole which is bored through the main body 2a to hold the elongated rod 11 with play.

Attachment holes 5 are bored on side walls of the groove 4 respectively for attachment of jigs.

The wedge-like member 6a is a short cylindrical member provided with a flange 7a on one end and with tapered portion 8a on the other end. A slit 9a is cut axially through the side wall of the cylindrical body and partially on the flange 7a, and no cylindrical body is knurled on its peripheral surface except for the tapered portion 8a, the flange 7a and a portion near the flange 7a.

The wedge-like member 6a has an outer diameter sufficient to allow forcible insertion of the retaining member 4b of the groove 4 of said hook member 2 and an internal diameter which allows the wedge member to be mounted from outside and made freely slidable thereon.

The elongated rod 11 preferably comprises a rod member having a perfectly circular cross-section of which the peripheral surface is not knurled but is formed smoothly. The rod may have a length and thickness appropriate for the intended correctional procedures. There is no specific condition about the dimension, but the diameter thereof is preferably approximately 7 mm and the length may vary from 6 to 40 cm.

The spinal deformity correction device 1 comprising above-mentioned hook members 2, wedge members 6a and an elongated rod 11 is preferably made of a metal having a strength suitable for a surgical device, e.g., stainless steel or an alloy of molybdenum-nickel-chromium and steel.

The procedure for using the spinal deformity correction device 1 will now be described.

The spine of the patient is exposed by a surgical operation, and two hook members 2, 2 of the device 1 are fixed at a predetermined interval with the patient's transversal projections, the spinal joints or arch of the deformed spine.

The engagement is secured with the hook engagement members 3 of the hook members 2. More particularly, the hook members 3 are hooked on the horizontal projections, spinal joints or arches of the spine of the patient at positions suitable for pulling and correcting the curved or deformed spine in a manner such that the curved openings of the members 3 face outward in opposite directions.

An outrigger device is then attached via a hook cover between engaged hooked members 2, 2 and the spine is gradually pulled or stretched within safe limits while the degree of pulling is adjusted and monitored by means of a torque wrench for the fixation. (The hook cover, the outrigger device and the torque wrench are not part of the claimed invention and are of any known type, hence they are not shown.)

Then, after the spine is pulled and corrected to a desired position by the outrigger device, the elongated rod 11 is attached between the hook members 2, 2 by passage respectively through the grooves 4, 4.

Two wedge members 6a, 6a are mounted in advance on the rod 11 with their tapered portions 8a, 8a opposing each other on opposite sides of a hook member 2. When the rod 11 is to be attached to the hook member 2, the member 2 is positioned between the tapered portions 8a, 8a of the wedge members 6a, 6a and the opening 4a of the member 2 is held on the side of the rod 11 and forced into it toward the member 4b so as to facilitate insertion thereof.

Figure 5:
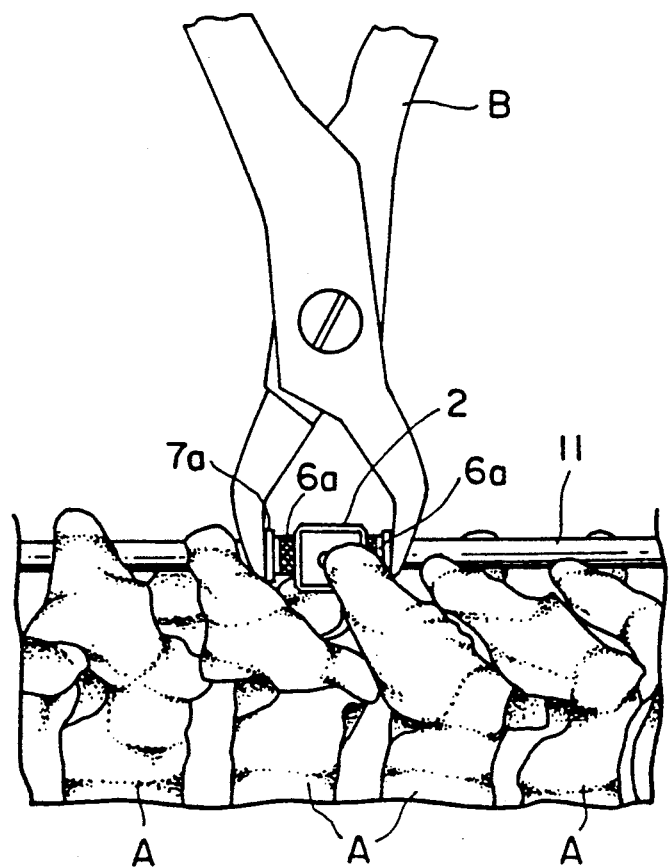
FIG. 5 is a partial frontal view to show the device in use.

In this state, the elongated rod 11 is positioned with a predetermined play within the hole or groove 4 of the member 2, and the hook member 2 is positioned between the wedge members 6a, 6a. By using a tool B, shown in FIG. 5, the flanges 7a, 7a of the wedge members 6a, 6a are pressingly moved toward the hook member 2 so as to be forcibly inserted from the tapered portions 8a, 8a into the groove inside the member 2.

Due to the tapered portions formed on ends of the wedges 6a, 6a, they are easily inserted into the interstices formed by the loose engagement provided by the predetermined play between the hook member 2 and the rod 11 passed therethrough.

The wedge members can be reduced in diameter during their insertion due to the slit 9a formed axially therein, so as to be easily forced into the hole or groove 4 and, at the same time, the knurled surface on the outer peripheral surface 10a tightly contacts the inner periphery of the member 4b of the hole or groove 4 to prevent detachment therefrom so that the rod 11 can be firmly fixed with the hook members 2.

The selected spacing between the hook members 2, 2 is thereafter maintained by the rod 11, to thereby sustain the pulled out state of the spine A.

The outrigger device is then removed, and openings on the patient's muscular tunics, the fascia, and the skin are sutured. By retaining the device fixed to the patient's spine for a certain period, an excellent correctional effect can be achieved.

Figure 6:
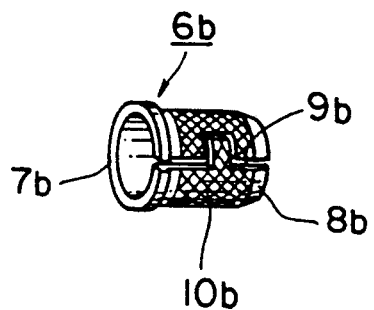
FIG. 6 is a perspective view to show another embodiment of the wedge member.
Figure 7:
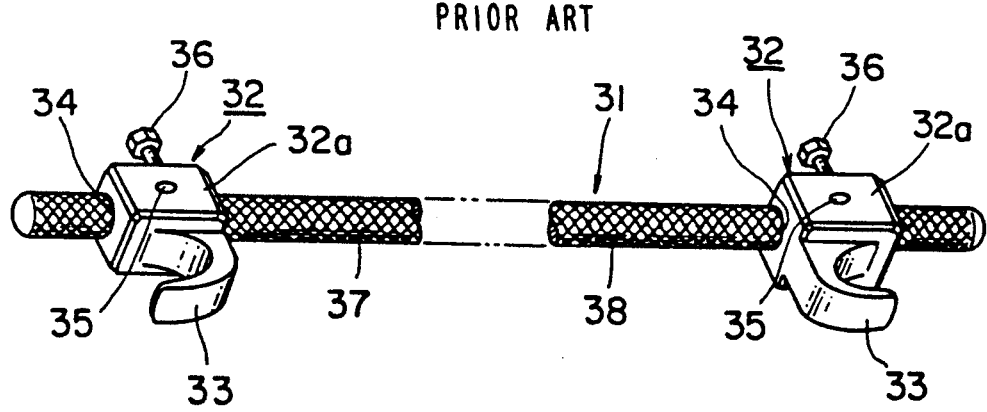
FIG. 7. is a perspective view of the assembled state of a prior art spinal deformity correction device.

The wedge member according to another preferred embodiment has a structure similar to that shown in FIG. 6. More particularly, wedge member 6b is a short cylindrical body provided with an engagement flange 7b in a manner similar to the wedge member 6a on one end and a tapered portion 8b on the other end, and is formed with another slit perpendicularly to the axial slit to form a crenellated slit 9b in the side wall and a part of the flange 7b extending therefrom. The peripheral surface except for the tapered member 8b and the flange 7b is knurled to form a roughened surface 10b.

The spinal deformity correction device according to this invention comprises an elongated rod with a smooth peripheral surface, hook members each having a retaining portion through which said rod is inserted with play and a hook engagement portion on one side thereof and cylindrical wedges with slits each having a flange on one end thereof. Plural hook members are hooked on the deformed spine and the spine is pulled. Under such a state, a rod is loosely inserted into the hook members and wedge members which have been mounted on said rod in advance are forcibly inserted into the interstices formed between loosely fitting hook members and the rod to thereby securely fix them.

As device having the above-mentioned structure does not have a knurled surface on the rod, it does not adversely affect the patient's body of on whom it is being used for spinal correction. Due to the use of the wedge members, the rod can be attached with the hook members simply and securely, and this greatly contributes to the reduction of operation time, enhancement of safety, and facilitation of the corrective procedure.

In this disclosure, there are shown and described only the preferred embodiments of the invention, but, as aforementioned, it is to be understood that the invention is capable of use in various other combinations and environments and is capable of changes or modifications within the scope of the inventive concept as expressed herein.

What is claimed is:

1. A device for correcting spinal deformities by attachment to a patient's spine for a predetermined period for correctively fixing the same, comprising:
   an elongated rod, having a smooth peripheral surface;
   a hook member, formed with a hook-like engagement member at one end and comprising a retaining portion through which said elongated rod is loosely inserted; and
   a wedge-like fixing member in the form of a hollow cylinder formed with a lengthwise slit, said cylinder having a flange at a first end and a taper at a second end,
   whereby said elongated rod is loosely inserted into said retaining portion of said hook member with a predetermined play and the fixing member mounted on the elongated rod is forcibly inserted at said tapered end thereof into an interstice formed between the loosely fitted rod and hook members to thereby firmly fix the hook member to the elongated rod.

2. A device for correcting spinal deformities as claimed in claim 1, wherein:
   said elongated rod is made of a rust-proof steel material.

3. A device for correcting spinal deformities as claimed in claim 1, wherein:
   said elongated rod has a diameter sufficient to endure a minimum compressive load of 60 kg in a deflection test.

4. A device for correcting spinal deformities as claimed in claim 1, wherein:
   said hook member is formed by molding a material similar to that of the elongated rod.

5. A device for correcting spinal deformities as claimed in claim 1, wherein:
   said fixing member is molded from a material similar to that of said elongated rod and hook member.

6. A device for correcting spinal deformities as claimed in claim 1 wherein:
   said cylinder of the wedge has a knurled peripheral surface.

7. A device for correcting spinal deformities and fixing the same as claimed in claim 1, wherein:
   said fixing member is formed to further comprise a tapered portion at said first end thereof.

8. A device for correcting spinal deformities as claimed in claim 1, wherein:
   said slit in said fixing member comprises an axially oriented portion and another portion oriented perpendicular thereto to form a crenellated slit in the side wall of the fixing member and in a part of said flange thereof.

9. A device for correcting spinal deformities as claim in claim 7, wherein:
   said slit in said fixing member comprises an axially oriented portion and another portion oriented perpendicular thereto to form a crenellated slit in the side wall of the fixing member and in a part of said flange thereof.

* * * * *